(12) United States Patent
Sindt (10) Patent No.: US 11,771,412 B2
(45) Date of Patent: Oct. 3, 2023

(54) EYELID FLIPPER TOOL

(71) Applicant: University of Iowa Research Foundation, Iowa City, IA (US)

(72) Inventor: Christine Sindt, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 169 days.

(21) Appl. No.: 16/335,710

(22) PCT Filed: Nov. 8, 2017

(86) PCT No.: PCT/US2017/060545
§ 371 (c)(1),
(2) Date: Mar. 22, 2019

(87) PCT Pub. No.: WO2018/089429
PCT Pub. Date: May 17, 2018

(65) Prior Publication Data
US 2020/0029950 A1    Jan. 30, 2020

Related U.S. Application Data

(60) Provisional application No. 62/420,631, filed on Nov. 11, 2016.

(51) Int. Cl.
*A61F 9/007* (2006.01)
*A61B 17/02* (2006.01)

(52) U.S. Cl.
CPC ...... *A61B 17/0231* (2013.01); *A61F 9/00718* (2013.01)

(58) Field of Classification Search
CPC .................................................. A61B 17/0231
See application file for complete search history.

(56) References Cited

U.S. PATENT DOCUMENTS

| | | | | | |
|---|---|---|---|---|---|
| 3,411,364 | A | * | 11/1968 | Horley | A61F 9/0061 73/818 |
| 3,910,618 | A | * | 10/1975 | Massenz | A61F 9/0061 606/107 |
| 4,036,230 | A | * | 7/1977 | Adams | A61F 9/0017 604/294 |
| 5,348,358 | A | * | 9/1994 | Selick | A61F 9/0061 294/902 |

(Continued)

FOREIGN PATENT DOCUMENTS

| | | | |
|---|---|---|---|
| JP | 2003304930 A | * | 10/2003 |
| KR | 20-0472398 | * | 4/2014 |

*Primary Examiner* — Zade Coley
(74) *Attorney, Agent, or Firm* — Smith Gambrell & Russell LLP (57) ABSTRACT

An eyelid flipper tool is used to flip a patient's eyelid to gain access to the patient's meibomian gland lands and gland openings. The eyelid flipper tool has a concave end and a convex end connected by a center section. The concave end has a concave edge with a concave end width, a concave radius, and a curvature. The convex end of the eyelid flipper tool has a convex edge with a convex end up with, a convex end radius, and a curvature. The radii of the concave end and the convex end and the curvature of the ends are dimensioned to conform to the curvature of the eyelids or the globe of a patient's eye.

2 Claims, 10 Drawing Sheets

(56) References Cited

U.S. PATENT DOCUMENTS

| | | | | |
|---|---|---|---|---|
| 5,941,873 | A * | 8/1999 | Korenfeld | A61F 9/008 606/4 |
| 7,402,156 | B2 * | 7/2008 | Kiehlbauch | A61F 9/0017 606/4 |
| 8,235,893 | B2 * | 8/2012 | Josephberg | A61B 17/0231 600/245 |
| 2002/0103421 | A1 * | 8/2002 | Putrino | A61B 17/0231 600/209 |
| 2008/0081952 | A1 * | 4/2008 | Josephberg | A61B 17/0231 600/245 |
| 2008/0082057 | A1 * | 4/2008 | Korb | A61B 3/101 604/289 |
| 2008/0114423 | A1 * | 5/2008 | Grenon | A61F 7/007 607/96 |
| 2008/0255578 | A1 * | 10/2008 | Neusidl | A61F 9/0017 606/107 |
| 2010/0274257 | A1 * | 10/2010 | Neusidl | A61F 9/0017 606/107 |
| 2014/0142663 | A1 * | 5/2014 | Van Valen | A61N 5/0616 607/88 |

* cited by examiner

FIG.15

EYELID FLIPPER TOOL

CROSS REFERENCE TO RELATED PATENT APPLICATIONS

This invention claims priority from U.S. Provisional Patent Application Ser. No. 62/420,631, filed Nov. 11, 2016, which is hereby incorporated by reference.

FIELD OF THE INVENTION

This invention relates to eyecare evaluations of the meibomian glands of a patient, and more particularly, relates to a tool for manipulating a patient's eyelids to provide better access to the patient's meibomian gland openings along the rims of the patient's eyelids.

BACKGROUND OF THE INVENTION

Meibomian gland disease is very common. The literature states that up to 70% of the population has meibomian gland disease. Meibomographers for evaluating meibomian gland disease are becoming more common in the average practice. Evaluation of the meibomian glands is difficult if the eyelid is not flipped evenly and into a single plane. Further, software to automatically analyze the meibomian glands will not operate properly unless the eyelids of the patient are flipped so that the meibomian glands lie in a single plane.

No tool currently exists that allows the practitioner to flip the patient's eyelids evenly and consistently so that the meibomian glands lie in a single plane along the rims of the patient's eyelids. Historically, doctors have used their fingers or cotton swabs to flip the patient's eyelids for access to the meibomian glands. Such procedures do not result in the eyelids being flipped so that the meibomian glands openings are in a single plane for examination and imaging.

SUMMARY OF THE INVENTION

The eyelid flipper tool of the present invention applies even pressure across the entire eyelid (upper and lower) causing the eyelid to evert. The eyelid flipper tool allows the eyelid to be flipped evenly and consistently so that the flipped eyelids of the patient lie in a single plane for evaluation and imaging.

In one embodiment, eyelid flipper tool of the present invention has a length with a longitudinal axis extending along the length of the eyelid flipper tool. The eyelid flipper tool has a concave end and a convex end connected by a center section. The concave end has a concave end width, a concave edge with a concave edge radius, and a concave end curvature about a longitudinal axis extending along the length of the eyelid flipper tool. The convex end has a convex end width, a convex edge with a convex edge radius, and a convex end curvature about a longitudinal axis extending along the length of the eyelid flipper tool.

In order to engage and evert a patient's eyelid, the concave end width, the concave edge radius, the concave end curvature about the longitudinal axis, the convex end width, the convex edge radius, and the convex end curvature about the longitudinal axis are dimensioned to conform to the dimensions of the eyelids or the globe of the patient's eye.

Further objects, features and advantages will become apparent upon consideration of the following detailed description of the invention when taken in conjunction with the drawings and the appended claims.

BRIEF DESCRIPTION OF THE DRAWINGS

FIG. 2a is a section view of the eyelid flipper tool in accordance with the present invention taken along line 2a-2a.

DETAILED DESCRIPTION OF THE PREFERRED EMBODIMENTS

Figure 1:
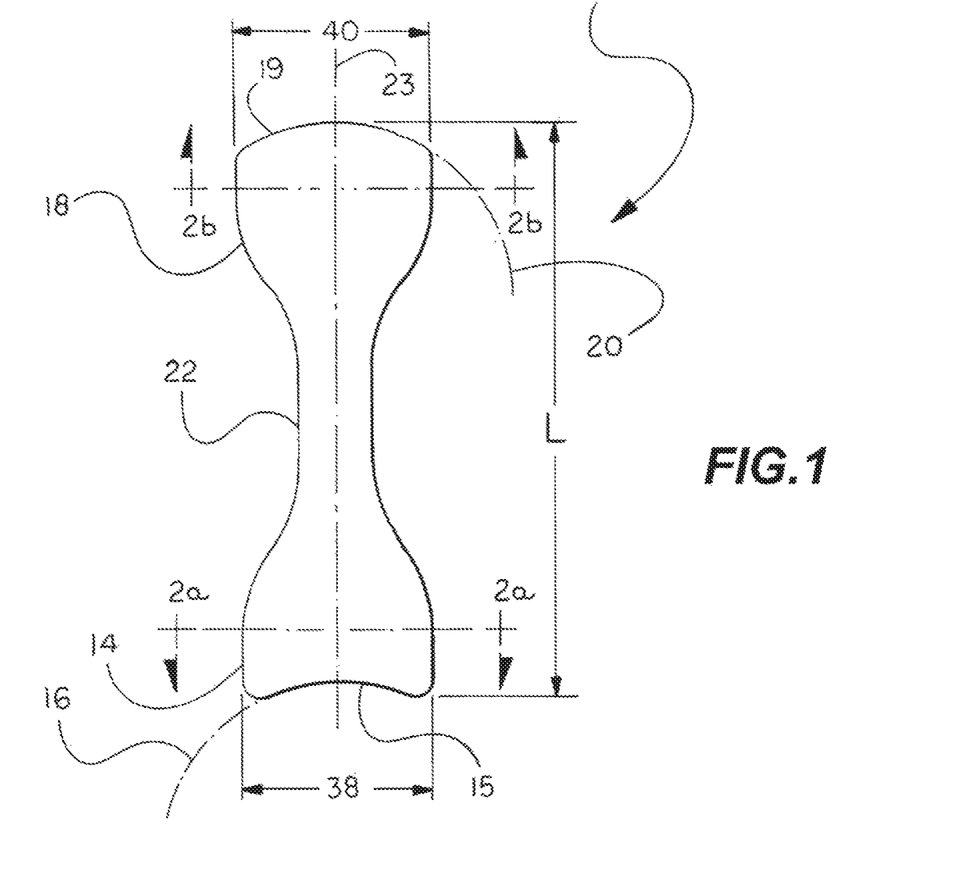
FIG. 1 is a top plan view of an eyelid flipper tool in accordance with the present invention.
Figure 2A:
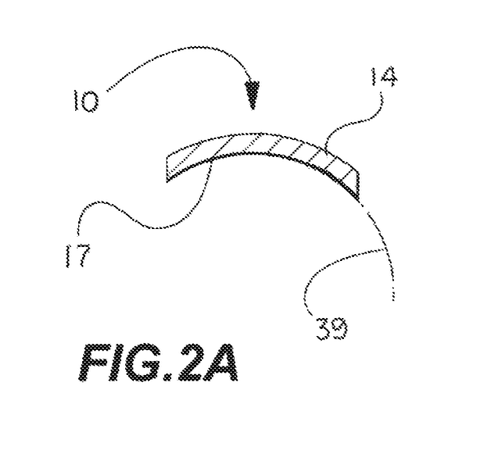
Figure 2B:
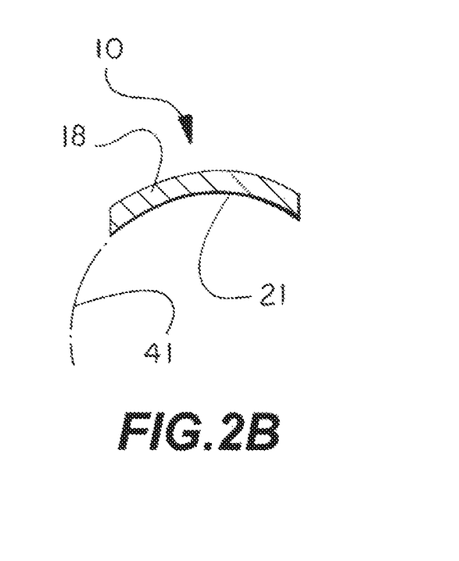
FIG. 2b is a section view of the eyelid flipper tool in accordance with the present invention taken along line 2b-2b.
Figure 3:
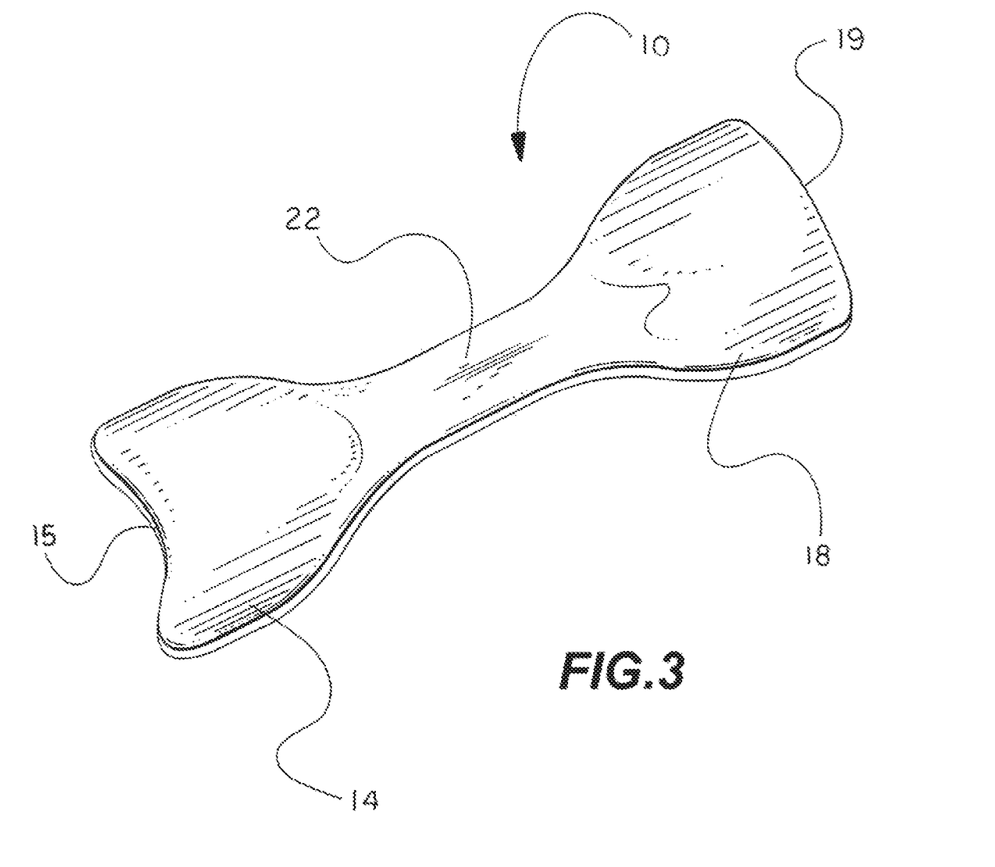
FIG. 3 is a top perspective view of the eyelid flipper tool in accordance with the present invention.

An eyelid flipper tool 10 in accordance with the present invention is shown in FIGS. 1-3. Other embodiments of the eye flipper tool 10 are shown in FIGS. 10-15. Use of the eyelid flipper tool 10 is illustrated in FIGS. 4-9.

With reference to FIGS. 1-3, one embodiment of the eyelid flipper tool 10 comprises a concave end 14 and a convex end 18 connected by a center section 22. The concave end 14 has a width 38 of between 0.75 and 1.5 inches, but the width 38 is typically 1.310 inch. The concave end 14 has a concave edge 15 with a concave edge radius 16. The concave edge radius 16 is between 0.75 and 1.5 inches, but the concave edge radius 16 is typically 1.125 inch. The concave edge radius 16 shown in FIG. 1 is dimensioned to conform generally to the radius and curvature of the eyelids 24 and 26 or the globe 30 of a patient's eye. While generally the concave edge 15 lies on the circumference of a circle with a single radius 16, the concave edge 15 may have a more complex curvature, such as an arc with multiple radii, all for the purpose of conforming concave edge 15 to the curvature of the eyelids 24 and 26 or the globe 30 of the patient's eye. With reference to FIG. 1 and FIG. 2a, the concave end 14 also has a concave end curvature 17 about a longitudinal axis 23. The concave end curvature 17 of the concave end 14 is also dimensioned to conform to the curvature of the eyelids 24 and 26 or the globe 30 of a patient's eye. The concave end curvature 17 has a curvature defined by a concave end curvature radius 39 between 0.75 and 1.5 inches, but typically has a curvature radius of 1.13 inch.

In the embodiment shown in FIGS. 1-3, the convex end 18 has a convex edge 19 with a convex edge radius 20. The convex end 18 has a width 40 of between 0.75 and 1.5 inches, but the width is typically 1.310 inch. The convex edge radius 20 is between 0.75 and 1.5 inches, but is typically 1.125 inch. The convex edge radius 20 shown in FIG. 1 is dimensioned to conform generally to the radius and curvature of the eyelids 24 and 26 or the globe 30 of a patient's eye. While generally the convex edge 19 lies on the circumference of a circle with a single convex edge radius 20, the convex edge 19 may have a more complex curvature, such as an arc with multiple radii, all for the purpose of conforming convex edge 19 to the curvature of the eyelids 24 and 26 or the globe of the patient's eye. With reference to FIG. 1 and FIG. 2b, the convex end 18 also has a convex end curvature 21 about the longitudinal axis 23. The convex end curvature 21 of the convex end 18 is also dimensioned to conform to the curvature of the eyelids 24 and 26 or the globe 30 of a patient's eye. The convex end curvature 21 has a curvature defined by convex end curvature radius 41 between 0.75 and 1.5 inches, but typically has a curvature radius of 1.13 inch.

In one embodiment, the eyelid flipper tool 10 is constructed of 316 stainless steel and has a thickness of 0.031 inch. Other suitable materials, which can be sterilized and have sufficient rigidity and smoothness, may be used to construct the eyelid flipper tool 10.

Figure 4:
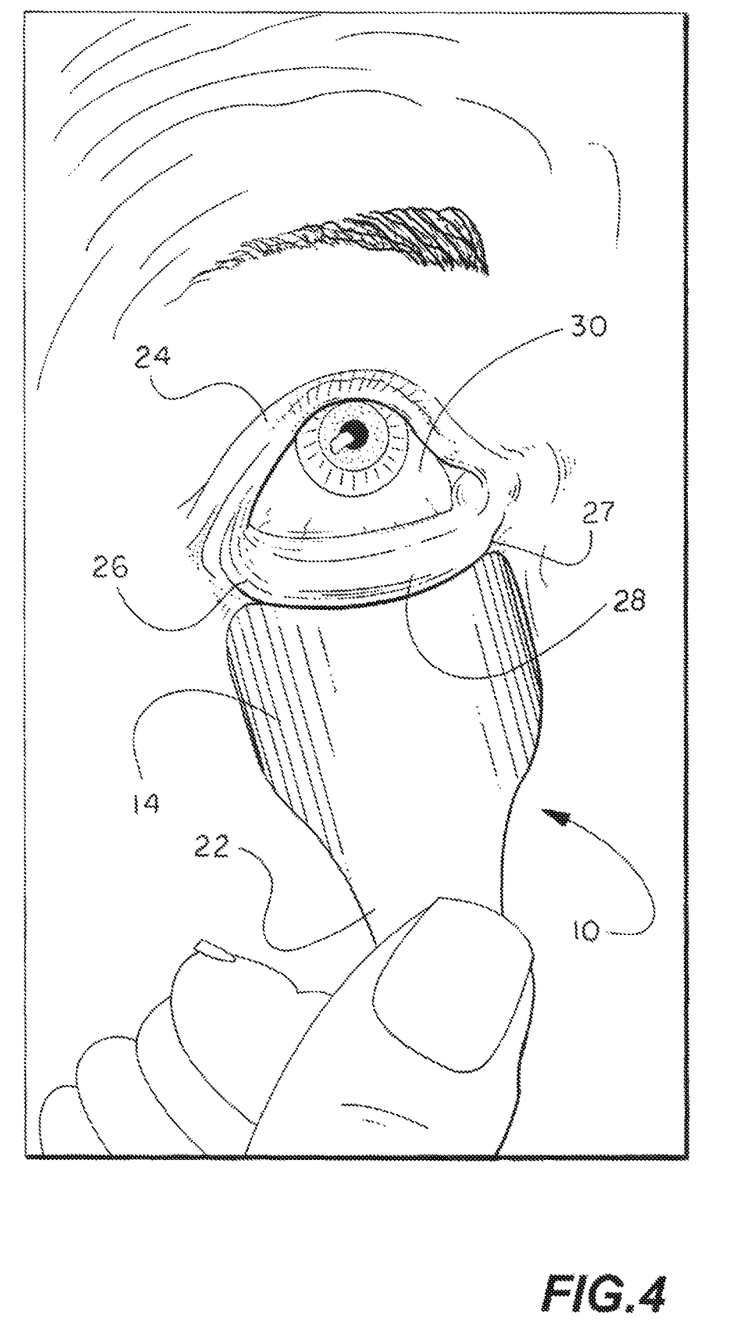
FIG. 4 is a perspective view showing the concave end of the eyelid flipper tool in use for lower eyelid eversion of a patient in accordance with the present invention.

FIG. 4 shows the concave edge 15 of the concave end 14 of the eyelid flipper tool 10 being used to evert the lower eyelid 26 of a patient in order to position the meibomian gland openings 28 in a single plane for examination and imaging. In order to evert the lower eyelid 26, the concave end 14 of the eye flipper tool 10 is positioned in engagement with the lower eyelid 26 just below the lower eyelid rim 27. A gentle upward pressure is then applied to the lower eyelid 26 until the lower eyelid 26 everts exposing the meibomian gland 28 in a single plane for examination and imaging.

Figure 5:
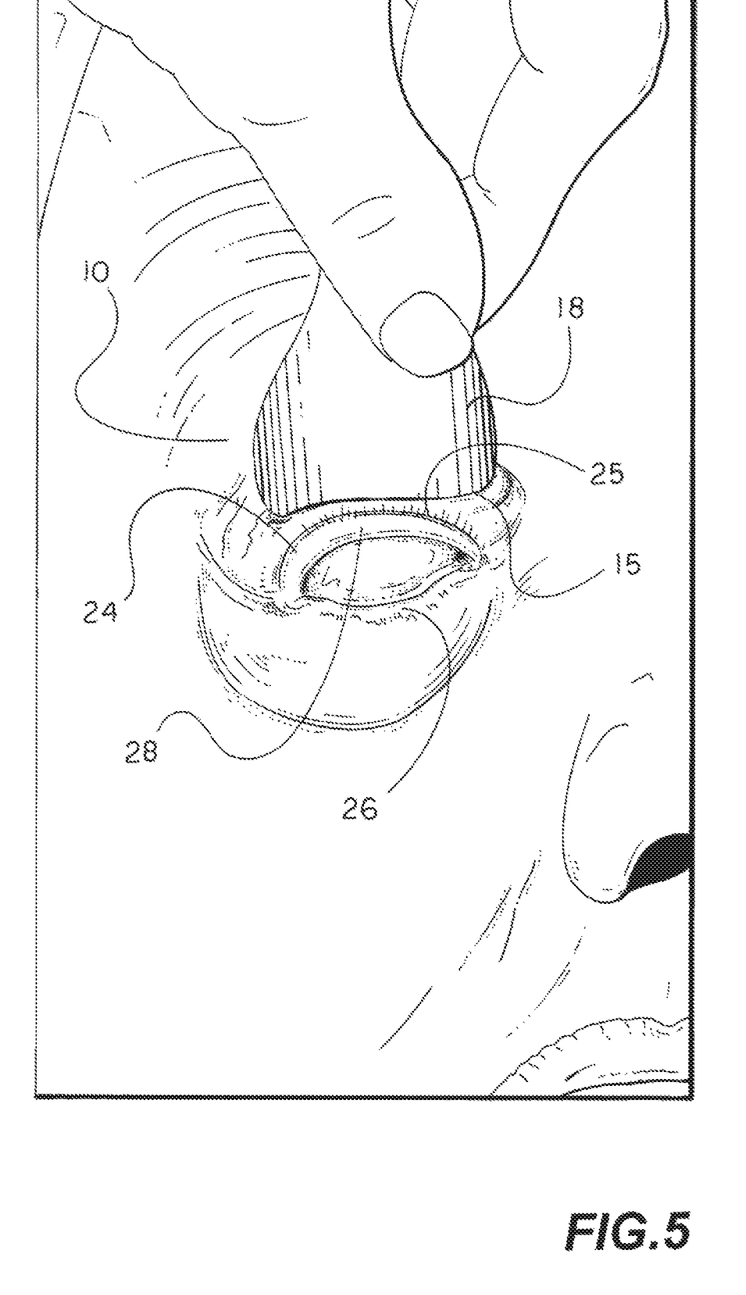
FIG. 5 is a perspective view showing the concave end of the eyelid flipper tool in use for upper eyelid eversion and stabilization of a patient in accordance with the present invention.

FIG. 5 shows the concave edge 15 of the concave end 14 of the eyelid flipper tool 10 being used to evert and stabilize the upper eyelid 24 of a patient in order to position the meibomian gland openings 28 in a single plane for examination and imaging. In order to evert the upper eyelid 24, the concave end 14 of the eye flipper tool 10 is positioned in engagement with the upper eyelid 24 just above the upper eyelid rim 25. A gentle downward pressure is then applied to the upper eyelid 24 until the upper eyelid 24 everts and is stabilized thereby exposing the meibomian gland 28 in a single plane for examination and imaging.

Figure 6:
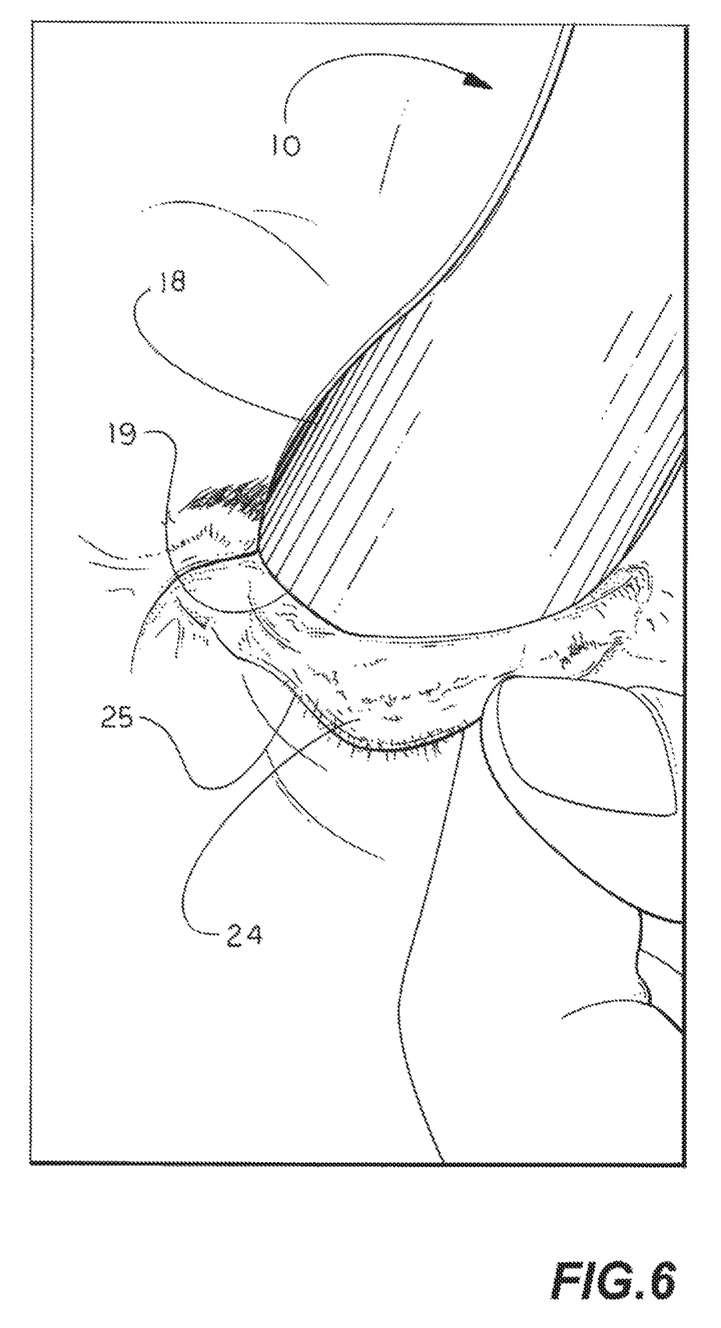
FIG. 6 is a perspective view showing the convex end of the eyelid flipper tool in use for upper eyelid eversion of a patient in accordance with the present invention.

FIG. 6 shows the convex edge 19 of the convex end 18 of the eyelid flipper tool 10 being used to evert and stabilize the upper eyelid 24. The convex edge 19 of the convex end 18 is positioned above the upper eyelid rim 25 the upper eyelid. The upper eyelid rim and 25 is then everted over the convex end 18 of the tool 10. Once the tarsal plate of the upper eyelid 24 has been rotated over the eyelid flipper tool 10 and stabilized, the meibomian gland openings are exposed in a single plane for examination and imaging.

Figure 7:
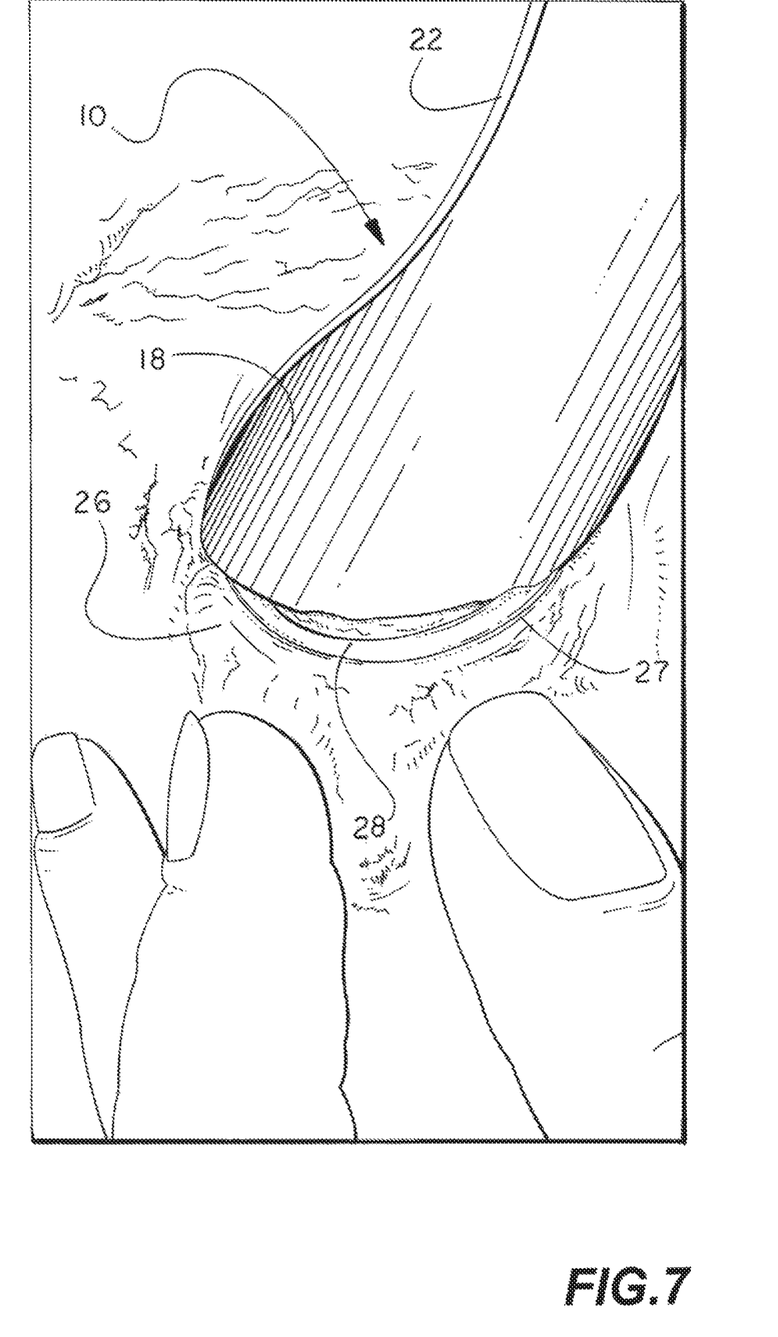
FIG. 7 is a perspective view showing the convex end of the eyelid flipper tool placed in the lower fornix of a patient's eye in accordance with the present invention.
Figure 8:
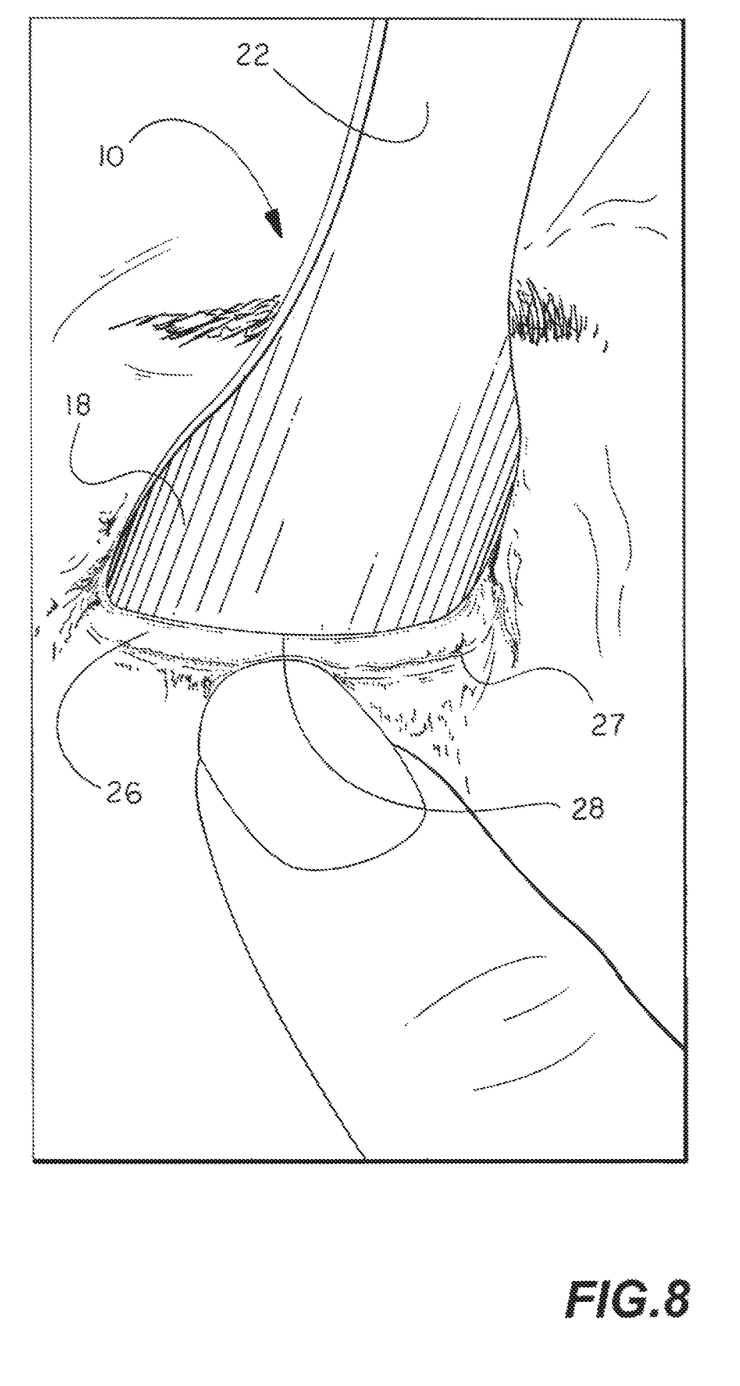
FIG. 8 is a perspective view showing the convex end of the eyelid flipper tool placed in the lower fornix of a patient's eye in accordance with the present invention.

FIGS. 7 and 8 show the convex edge 19 of the convex end 18 of the eyelid flipper tool 10 being inserted into the lower fornix of the lower eyelid 26 and against the globe 30 so that pressure can be applied adjacent to the meibomian gland in order to express meibum from the meibomian gland openings 28.

Figure 9:
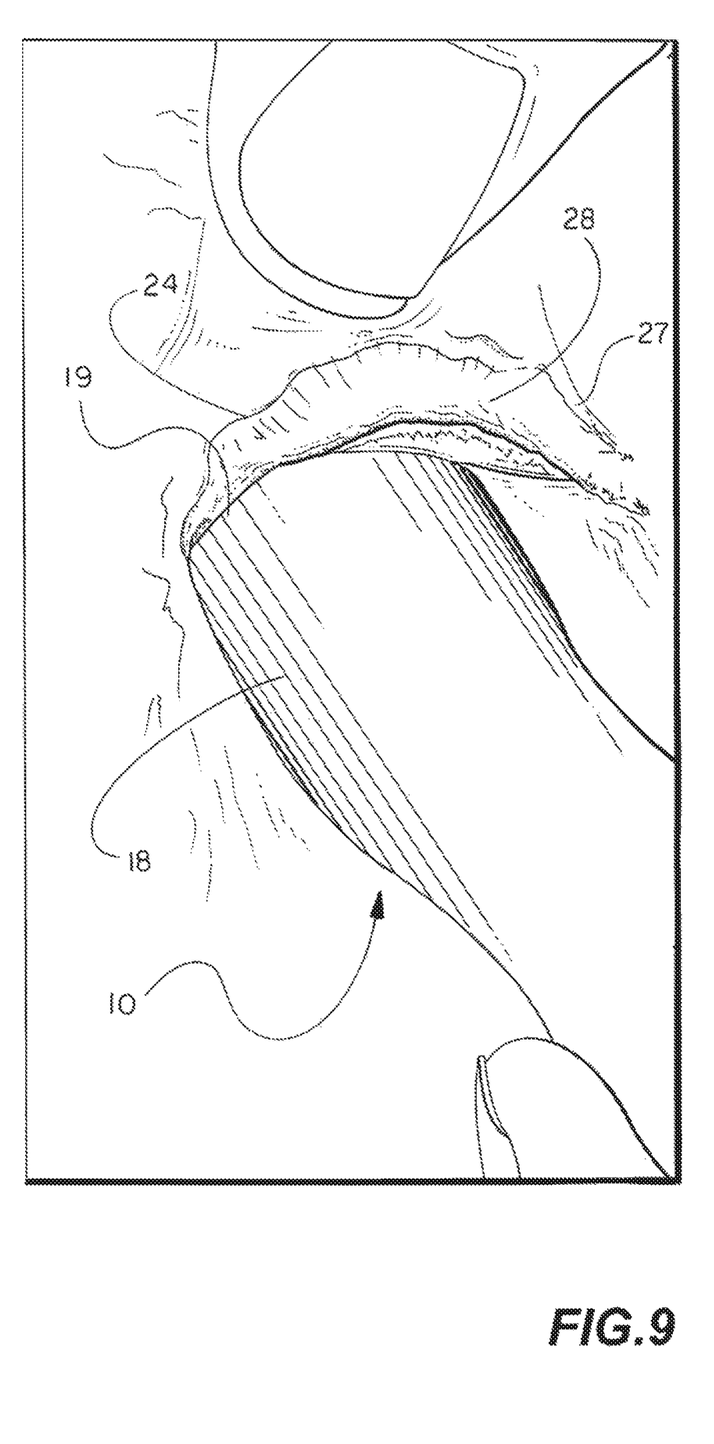
FIG. 9 is a perspective view showing the convex end of the eyelid flipper tool placed under the upper eyelid to pull the upper eyelid away from the globe in accordance with the present invention.
Figure 10:
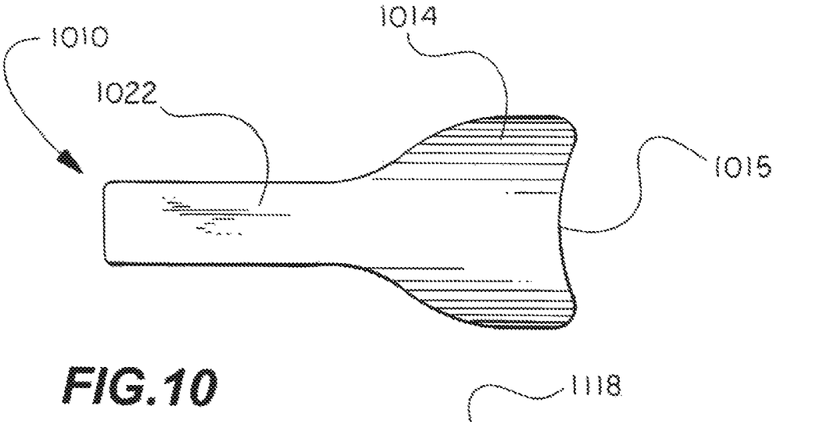
FIG. 10 is a top plan view of another embodiment of the eyelid flipper tool in accordance with the present invention.

FIG. 9 shows the convex edge 19 of the convex end 18 being inserted between the upper eyelid 28 and the globe 30 so that pressure can be applied adjacent to the meibomian gland in order to express meibum from the meibomian gland openings 28.

Figure 11:
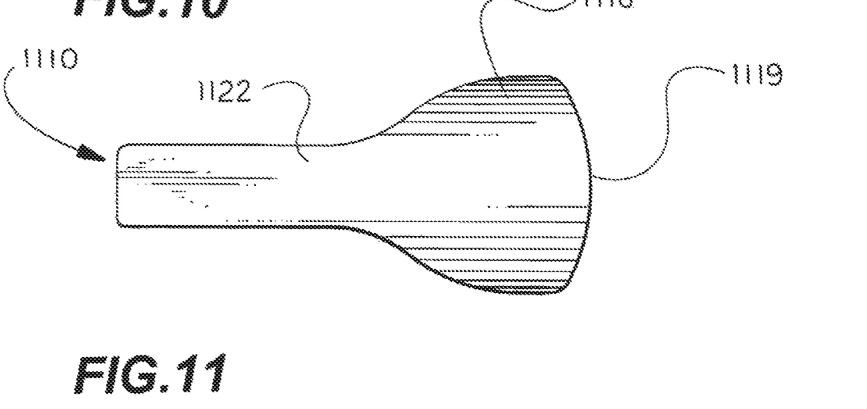
FIG. 11 is a top plan view of another embodiment of the eyelid flipper tool in accordance with the present invention.

In another embodiment of the present invention, a kit includes a concave eyelid flipper tool 1010 (FIG. 10) and a convex eyelid flipper tool 1110 (FIG. 11). The eyelid flipper tool 1010 comprises a concave end 1014 and a handle 1022. As previously described in connection with the eye flipper tool 10, the concave end 1014 has a width of between 0.75 and 1.5 inches, but the width is typically 1.310 inch. The concave end 1014 has a concave edge 1015 with a concave edge radius. The concave edge radius is between 0.75 and 1.5 inches, but the concave edge radius is typically 1.125 inch. The concave edge radius is dimensioned to conform generally to the radius and curvature of the eyelids 24 and 26 or the globe 30 of a patient's eye. While generally the concave edge 1015 lies on the circumference of a circle with a single radius, the concave edge 1015 may have a more complex curvature, such as an arc with multiple radii, all for the purpose of conforming concave edge 1015 to the curvature of the eyelids 24 and 26 or the globe 30 of the patient's eye. The concave end 1014 also has a concave end curvature about the longitudinal axis as previously described with respect to eyelid flipper tool 10. The concave end curvature of the concave end 1014 is also dimensioned to conform to the curvature of the eyelids 24 and 26 or the globe 30 of a patient's eye. The concave end curvature has a curvature defined by a radius between 0.75 and 1.5 inches, but typically has a curvature radius of 1.13 inch.

The convex end 1118 of the tool 1110 has a convex edge 1119 with a convex edge radius. The convex end 1118 has a width of between 0.75 and 1.5 inches, but the width is typically 1.310 inch. The convex edge radius is between 0.75 and 1% 5 inches, but is typically 1.125 inch. The convex edge radius is dimensioned to conform generally to the radius and curvature of the eyelids 24 and 26 or the globe 30 of a patient's eye. While generally the convex edge 1119 lies on the circumference of a circle with a single convex edge radius, the convex edge 1119 may have a more complex curvature, such as an arc with multiple radii, all for the purpose of conforming convex edge 1119 to the curvature of the eyelids 24 and 26 or the globe of the patient's eye. The convex end 1118 also has a convex end curvature as previously described in connection with the eye flipper tool 10. The convex end curvature of the convex end 18 is also dimensioned to conform to the curvature of the eyelids 24 and 26 or the globe 30 of a patient's eye. The convex end curvature has a curvature defined by radii between 0.75 and 15 inches, but typically has a curvature radius of 1.13 inch.

Figure 12:
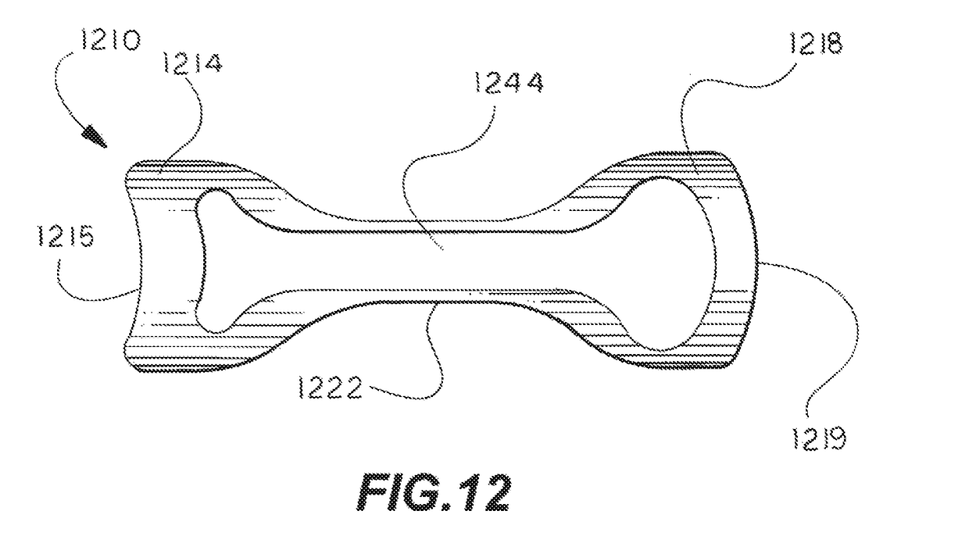
FIG. 12 is a top plan view of another embodiment of the eyelid flipper tool in accordance with the present invention.
Figure 13:
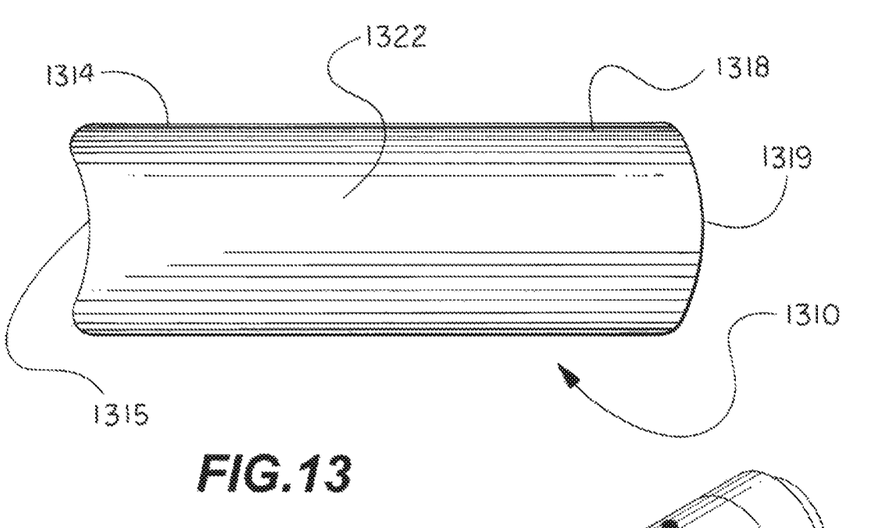
FIG. 13 is a top plan view of another embodiment of the eyelid flipper tool in accordance with the present invention.

Additional variations of the eyelid flipper tool 10 are shown in FIGS. 12 and 13. In FIG. 12, the eyelid flipper tool 1210 has a portion 1244 of the concave end 1214, the convex end 1218 convex, and the center section 1222 removed. In another variation shown in FIG. 13, the center section 1322 of the eyelid flipper tool 1310 has a constant width matching the width of the concave end width and the convex end width.

Figure 14:
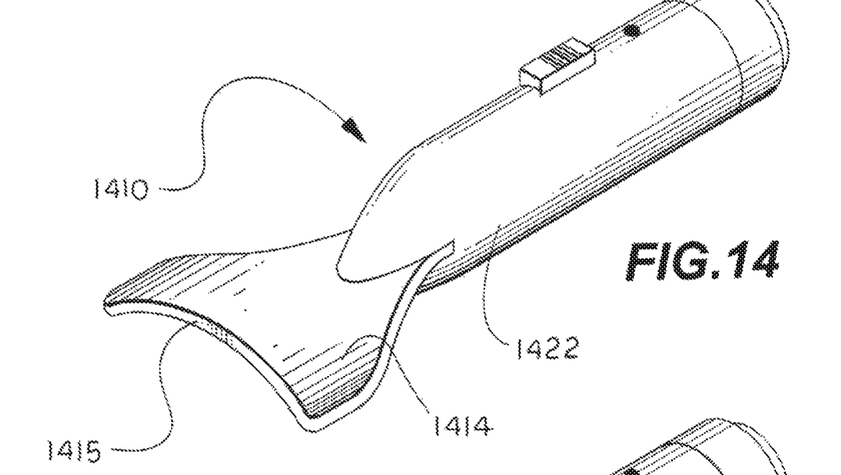
FIG. 14 is a perspective view of another embodiment of the eyelid flipper tool in accordance with the present invention.

A further feature of the eye flipper tool is illustrated in FIG. 14. FIG. 14 illustrates an eye flipper tool 1410 including a handle 1422 and a concave end 1414. The concave end 1414 has a concave end width, a concave edge 1415, a concave edge radius, and a concave end curvature. The concave edge 1415 is fitted with a heating element and/or a vibrating element. A battery in the handle 1422 provides power for the heating element and/or the vibrating element of the concave edge 1415. The heating element and vibrating element provide additional comfort when the concave edge 1415 engages the patient's eyelid or eye globe.

Figure 15:
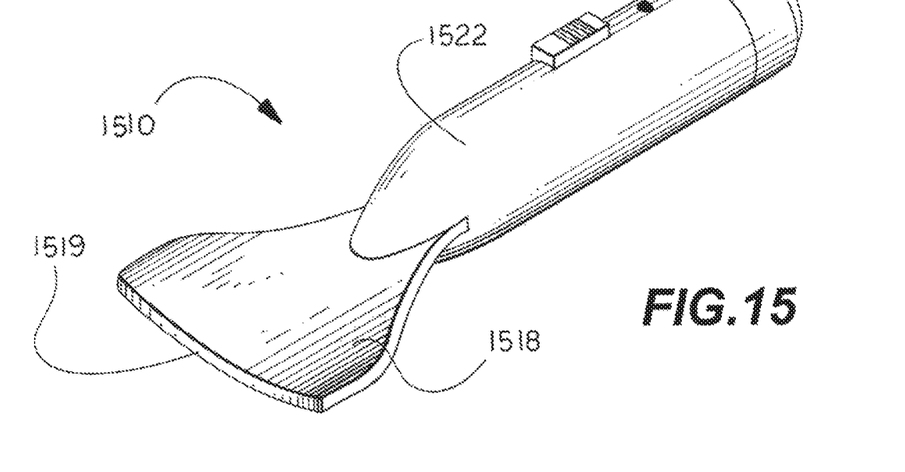
FIG. 15 is a perspective view of another embodiment of the eyelid flipper tool in accordance with the present invention.

FIG. 15 illustrates an eye flipper tool 1510 including a handle 1522 and a convex end 1518. The convex end 1518 has a convex end width, a convex edge 1519, a convex edge radius, and a convex end curvature. The convex edge 1519 is fitted with a heating element and/or a vibrating element. A battery in the handle 1522 provides power for the heating element and/or the vibrating element of the convex edge 1519. The heating element and vibrating element provide additional comfort when the convex edge 1519 engages the patient's eyelid or eye globe.

While this invention has been described with reference to preferred embodiments thereof, it is to be understood that variations and modifications can be affected within the spirit and scope of the invention as described herein and as described in the appended claims.

I claim:

1. An eyelid flipper tool for manipulating an eyelid with respect to a globe of an eye, the eyelid flipper tool having a length and comprising:
   a. a concave end having:
      i. a concave edge surface with a concave edge radius,
      ii. a concave end width, and
      iii. a partial concave end curvature surface with a concave end curvature radius; and
   b. a convex end having:
      i. a convex edge surface with a convex edge radius,
      ii. a convex end width, and
      iii. a partial convex end curvature surface with a convex end curvature radius; and
   c. a center section connecting the concave end and the convex end together, wherein the concave end width, the concave edge radius, and the partial concave end curvature radius are dimensioned to conform to the eyelid or globe of the eye, and
   wherein the convex end width, the convex edge radius, and the partial convex end curvature radius are dimensioned to conform to the eyelid or globe of the eye.

2. The eyelid flipper tool of claim 1, wherein the concave end has, a concave end width between 0.75 and 1.5 inches, a concave end radius between 0.75 and 1.5 inches, and a partial concave end curvature radius between 0.75 and 1.5 inches, and wherein the convex end has a convex end width between 0.75 and 1.5 inches, a convex end radius between 0.75 and 1.5 inches, and a partial convex end curvature radius between 0.75 and 1.5 inches.

* * * * *